United States Patent [19]

Fedotov

[11] Patent Number: 5,188,636

[45] Date of Patent: Feb. 23, 1993

[54] PURSE STRING SUTURE INSTRUMENT

[75] Inventor: Vladimir Fedotov, Moscow, U.S.S.R.

[73] Assignee: Ethicon, Inc., Somerville, N.J.

[21] Appl. No.: 880,943

[22] Filed: May 7, 1992

[51] Int. Cl.$^5$ .............................................. A61B 17/00
[52] U.S. Cl. ................................... 606/144; 606/139; 606/151; 606/157
[58] Field of Search ............... 606/139, 144, 148, 120, 606/157, 158, 151; 227/19; D24/145

[56] References Cited

U.S. PATENT DOCUMENTS

| | | | |
|---|---|---|---|
| D. 322,478 | 12/1991 | Green et al. | D24/145 |
| 4,345,600 | 8/1982 | Rothfuss | 128/334 R |
| 4,773,420 | 9/1988 | Green | 128/334 R |
| 4,821,939 | 4/1989 | Green | 227/19 |
| 4,915,107 | 4/1990 | Rebuffat et al. | 606/144 |

*Primary Examiner*—Stephen C. Pellegrino
*Assistant Examiner*—Gary Jackson
*Attorney, Agent, or Firm*—Paul A. Coletti; Charles P. Boukus

[57] ABSTRACT

A surgical instrument for applying purse string sutures to human tissue includes a pair of jaws on which a plurality of teeth are configured to firmly grip the tissue to be sutured and to pinch the tissue into a desirable configuration to receive the purse string sutures. The successive teeth on each jaw are alternately pointed and smooth with the pointed teeth on each jaw being opposed to the smooth teeth on the other jaw. A needle passage extends through the teeth on each jaw for guiding a needle attached to each purse string suture through the tissue which extends into the valleys on opposite sides of the teeth. A needle retainer is provided on each of the jaws for capturing the needles advanced through the needle passages. The needles are advanced by a pair of tubular sleeves which slide through the passages and receive the purse string sutures therein to guard the sutures against damage as the needles are advanced to draw the sutures through the passages. The tubular sleeves are attached to actuators which are operable simultaneously or independently so that one or more purse string sutures can be selectively applied to the tissue.

34 Claims, 7 Drawing Sheets

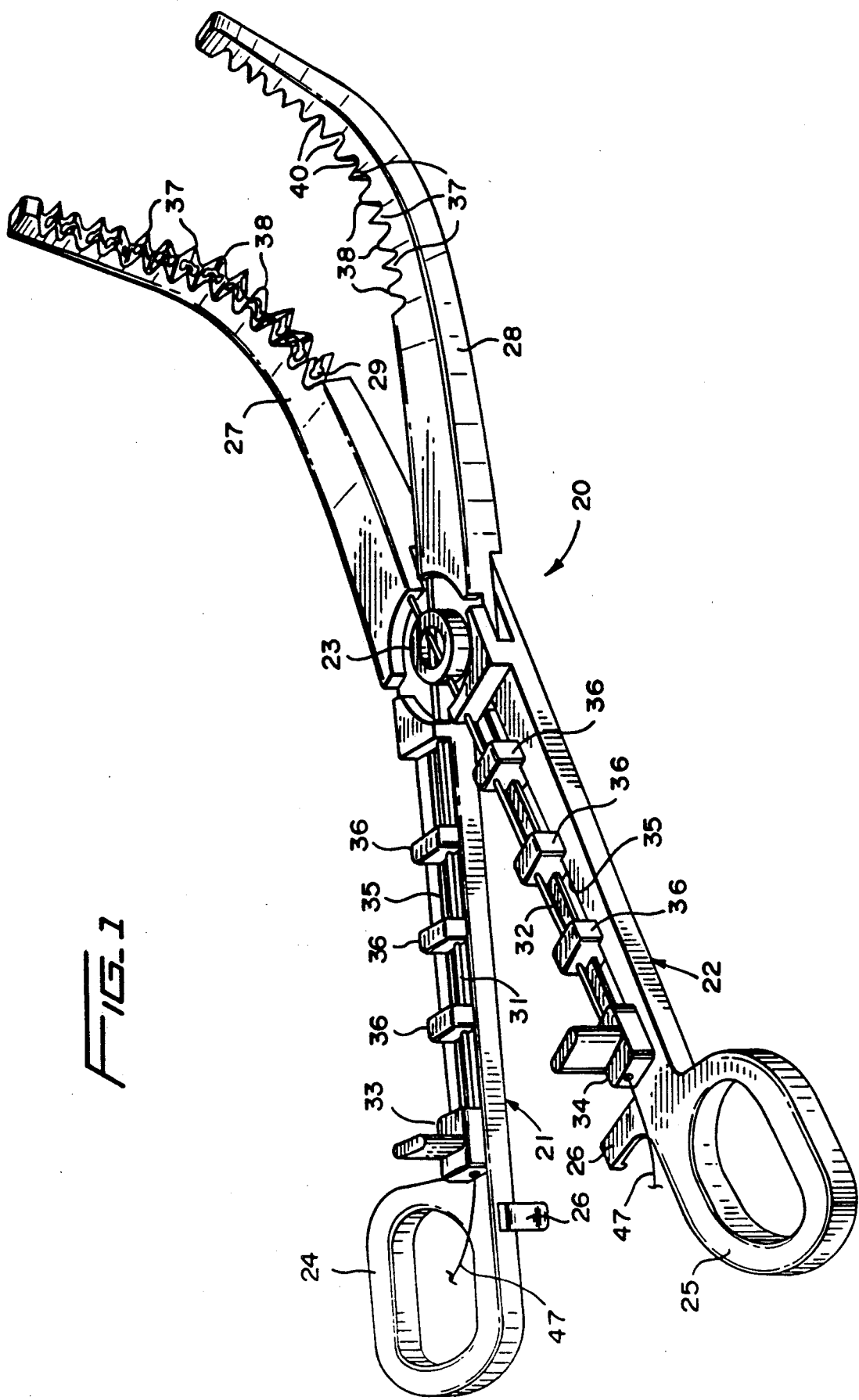

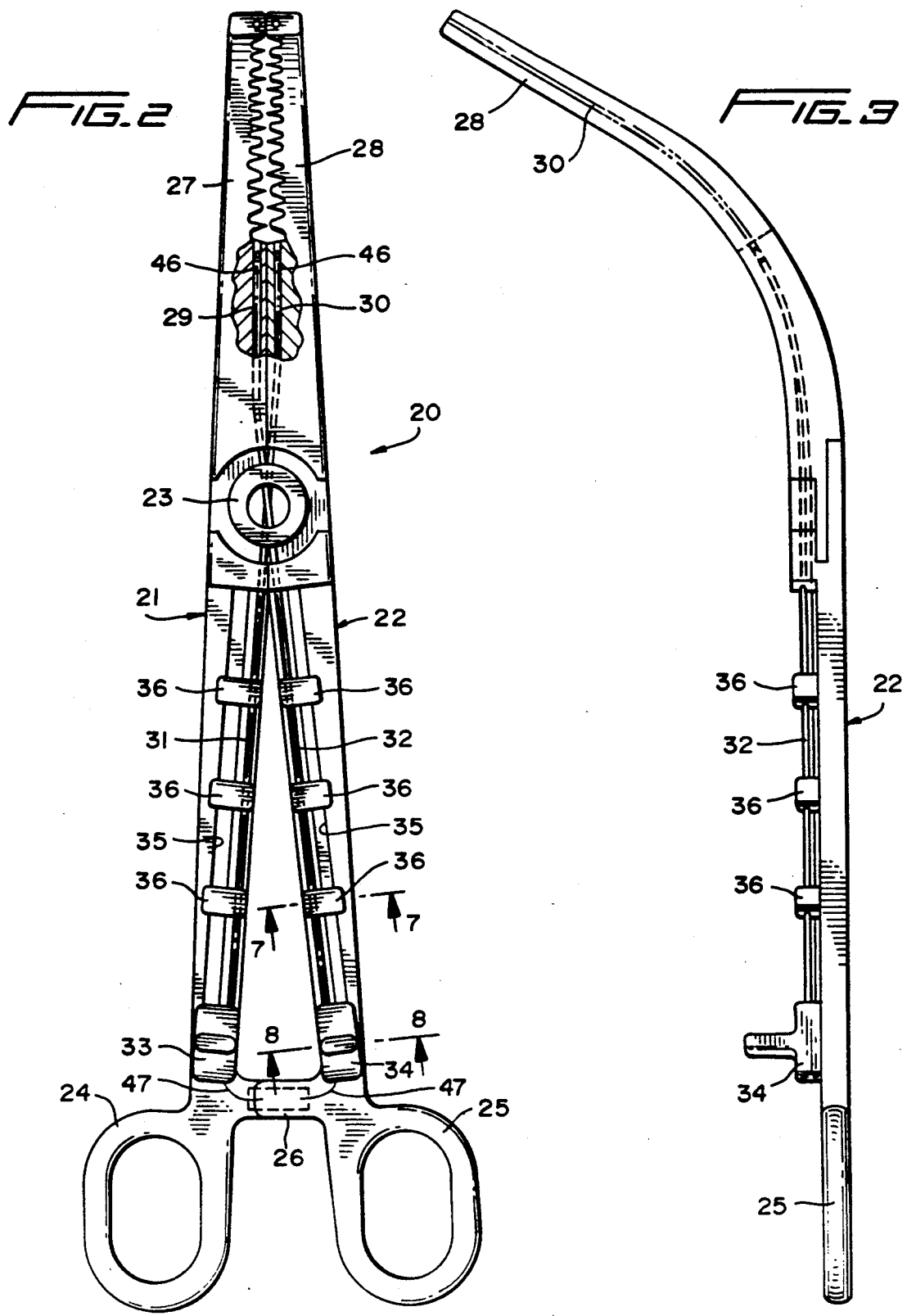

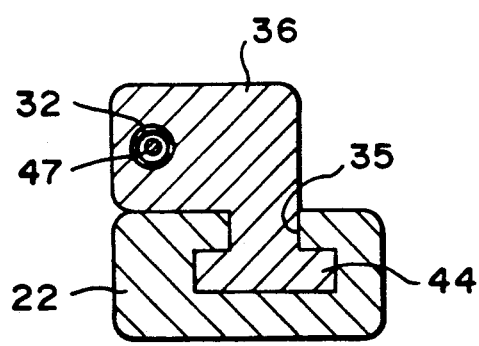
FIG_7
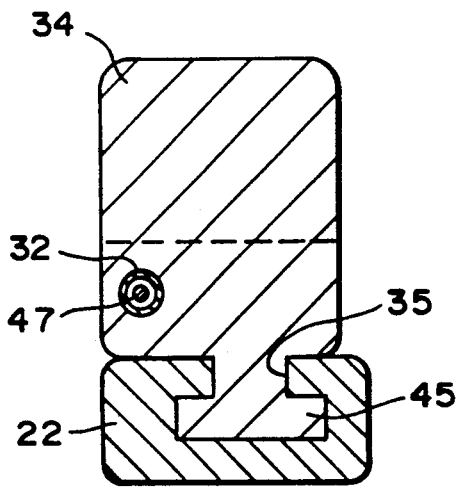
FIG_8
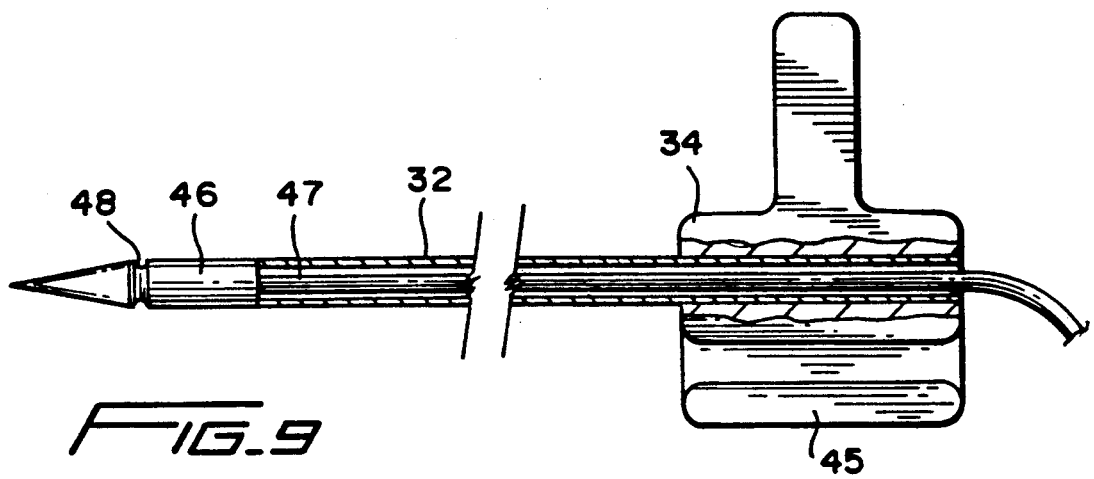
FIG_9
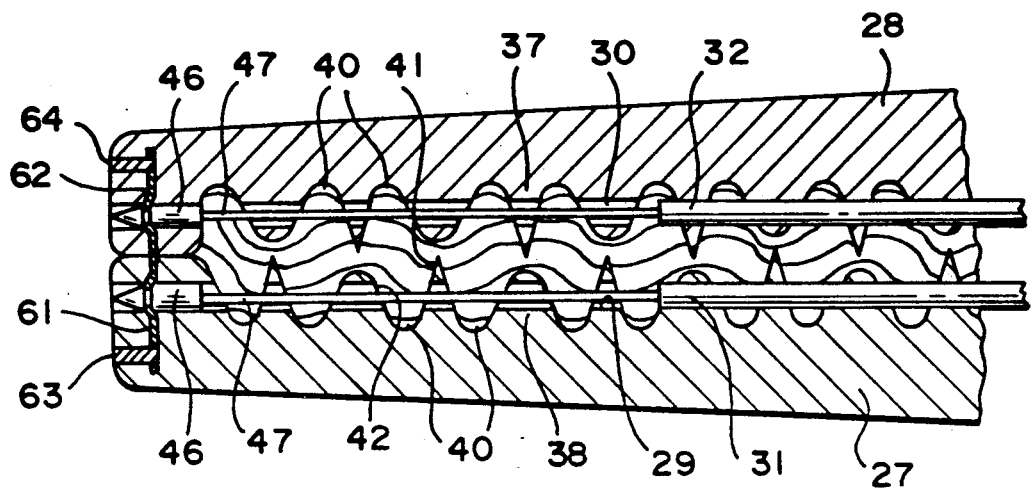
FIG_10

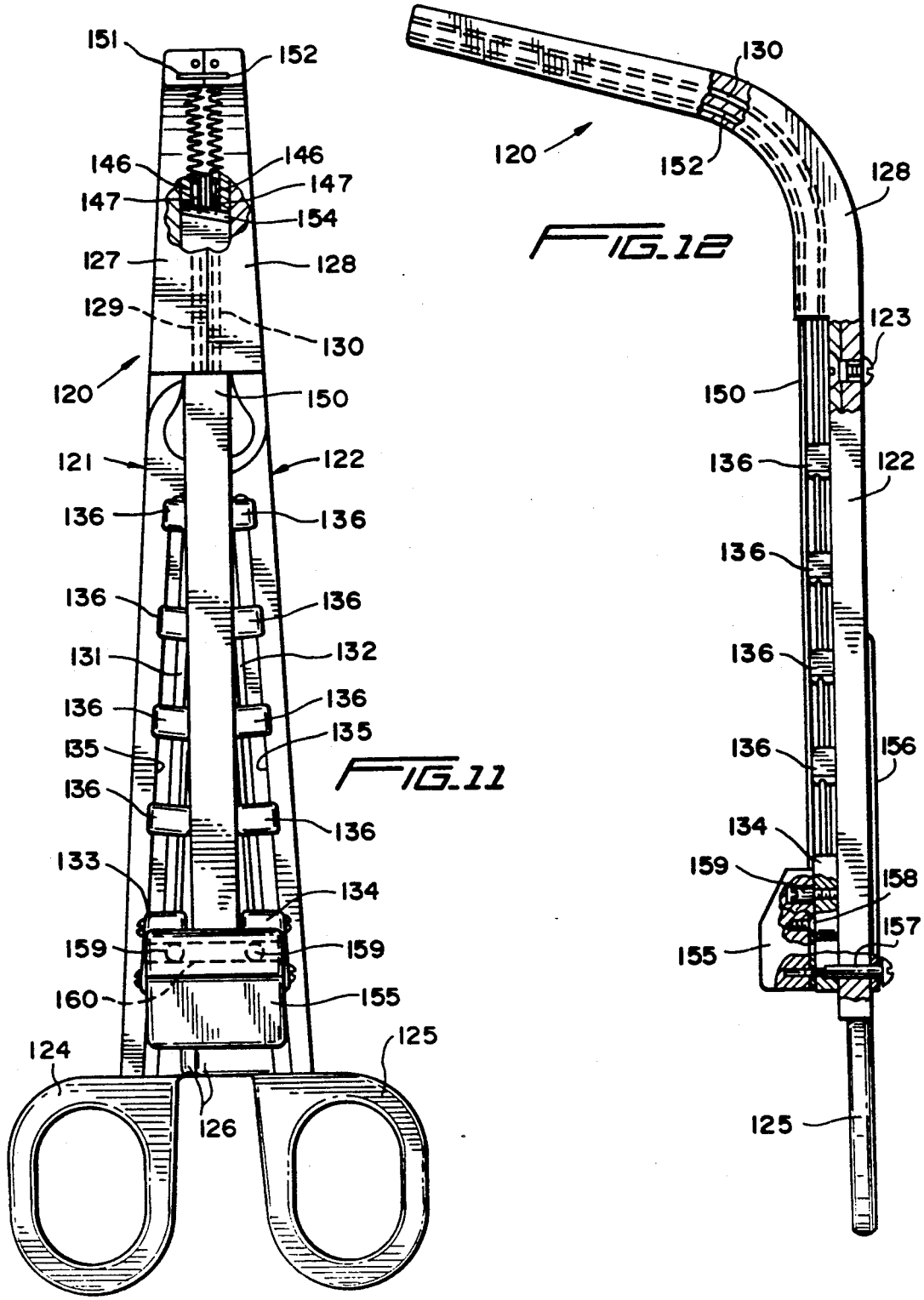

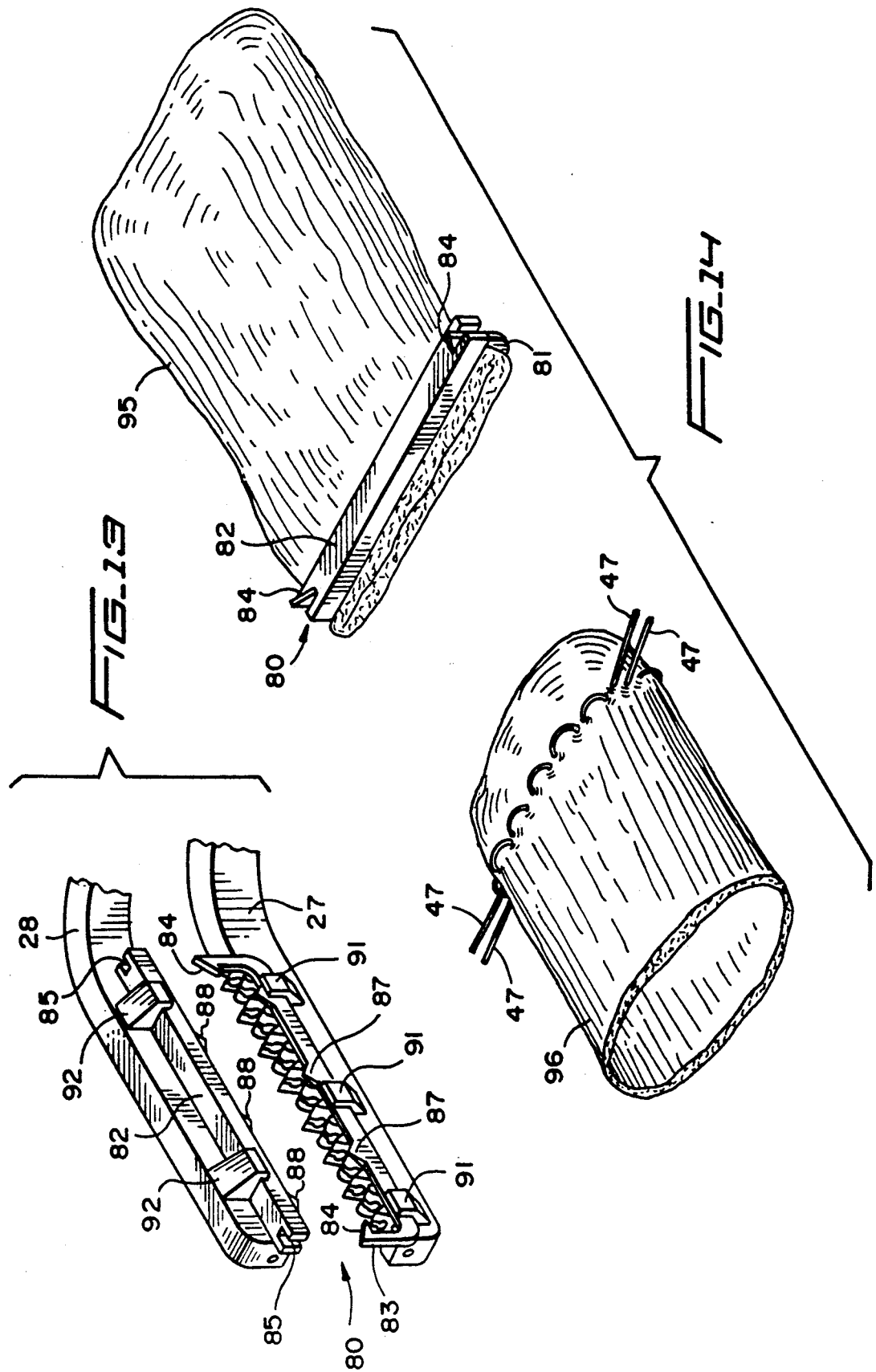

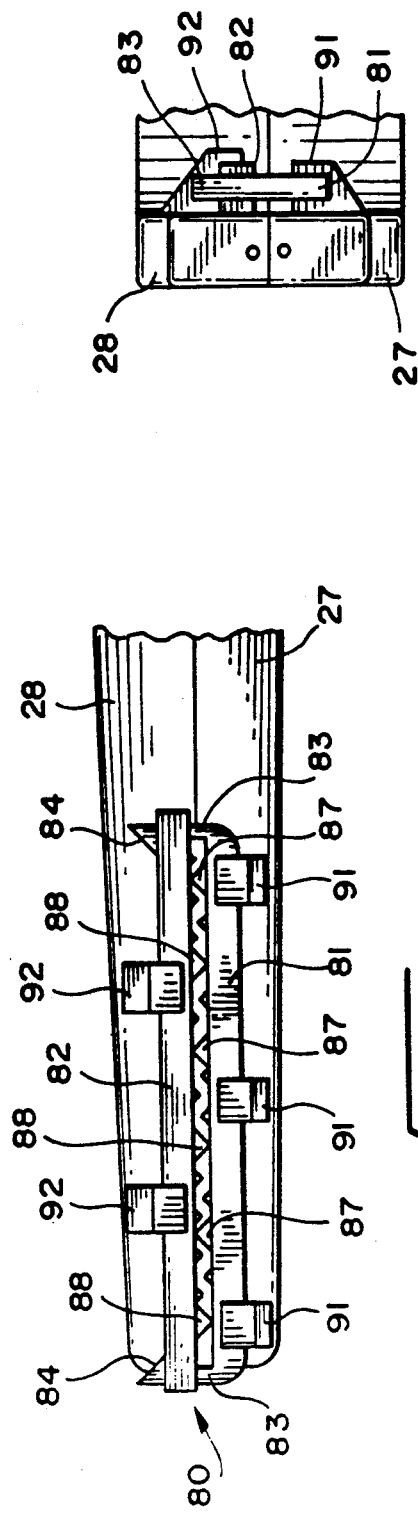
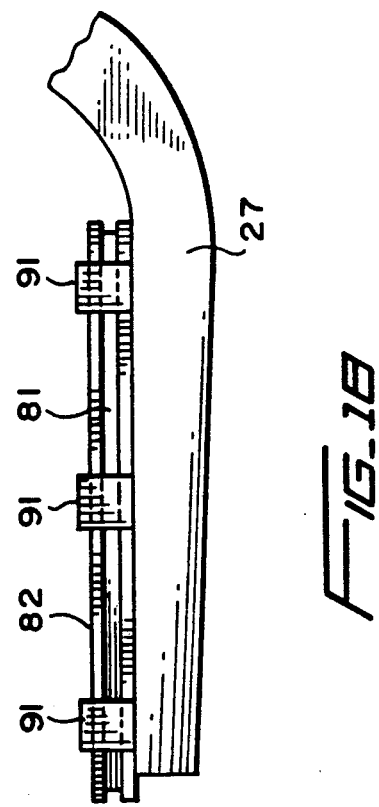
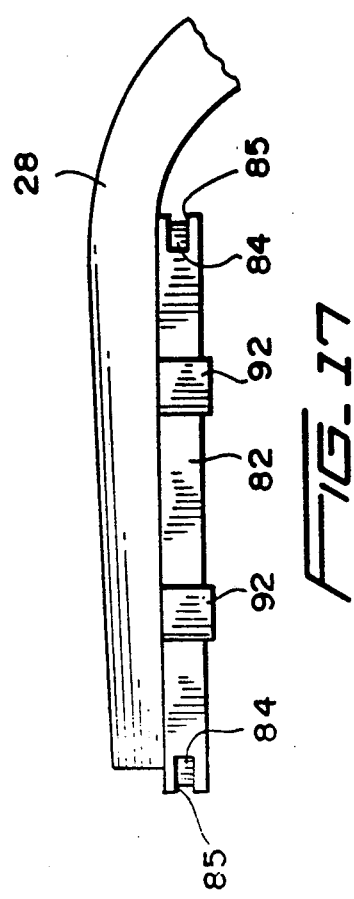

PURSE STRING SUTURE INSTRUMENT

BACKGROUND OF THE INVENTION

1. Field of the Invention

The present invention generally relates to a surgical instrument for applying purse string sutures to tissue and, more particularly, to a surgical instrument for applying purse string sutures to tubular tissue without the need for a surgeon to manually insert the suture needles into the instrument during the performance of surgery. Moreover, this invention relates to a purse string suture instrument provided with a pair of tissue clamping jaws which are adapted to firmly grip and shape the tissue into an appropriate configuration to be sutured and which capture the suture needles after the sutures are threaded into the tissue. Also, this invention relates to a purse string suture instrument which incorporates a knife blade for cutting the tissue adjacent to the purse string sutures threaded therein. Further, this invention concerns a purse string suture instrument provided with a tissue clamp which is applied to the tissue when the instrument is operated.

2. Description of the Prior Art

Purse string suture devices are known in the prior art which comprise a pair of serrated tissue clamping jaws provided with teeth for clamping the tissue to be sutured therebetween. Such devices include needle passages which extend through the teeth on each jaw for receiving a needle attached to a suture to be threaded through the tissue. In use, the tissue to be sutured is clamped between the jaws and the needle is manually passed through the needle passages in both jaws to thread the suture through the tissue. Thereafter, the jaws are opened and the purse string suture is tightened and wrapped to draw the tissue together. With this type of device, a considerable amount of manual effort and dexterity is required to accomplish the purse string suturing technique. Also, in such devices, it is difficult to control the flow of tissue between the teeth because an insufficient amount of space is provided to gather the tissue clamped by the jaws.

In the prior art, it has been proposed to provide automatic surgical instruments for applying the purse string sutures. For example, U.S. Pat. No. 4,915,107 discloses a purse string suture instrument in which a pair of needles attached to suture threads are driven through needle passages in the tissue clamping jaws by a pair of wires advanced simultaneously from rotatable drums. The tissue clamping jaws include teeth which are rectangular in configuration and separated by rectangular spaces. In use, it is desired that a sufficient amount of tissue be pinched into the spaces between the teeth to receive the needles and suture threads which are driven through the passages in the jaws. However, it appears that only a limited amount of tissue can be pinched into the path of the needles because of the rectangular configuration of the teeth and the rectangular spaces therebetween. Thus, it is possible that an insufficient amount of tissue may be gathered into the spaces between the teeth to properly perform the purse string suturing technique. Nor is any provision made to protect the sutures from damage as the needles are advanced through the passages in the teeth. Thus, the purse string sutures are exposed to possible damage or breakage as the sutures are drawn through the passages in the teeth. Also, no provision is made to capture the needles after being driven through the passages. Thus, after operating the instrument, the surgeon must manually retrieve the needles to locate the purse string sutures.

Accordingly, it is desirable to provide a surgical instrument for applying purse string sutures in which the tissue clamping jaws gather a sufficient amount of tissue into the spaces between the teeth to receive the purse string sutures. Also, it is desirable to provide a purse string suture instrument which operates automatically and captures the needles after advancement through the needle passages to allow the needles and sutures to be conveniently retrieved by the surgeon. Further, it is desirable to provide a purse string suture instrument which guards the purse string sutures against damage as the sutures are drawn through the passages in the teeth.

In addition, it is advantageous to provide a purse string suture instrument which incorporates a knife blade to sever the tissue adjacent to the purse string sutures threaded into the tissue. Additional advantages can be achieved by a purse string suture instrument provided with a tissue clamp which is applied to the tissue when the instrument is operated.

SUMMARY OF THE INVENTION

The present invention achieves an improved surgical instrument for applying purse string sutures to human tissue. The purse string suture instrument includes a pair of jaws on which a plurality of teeth are configured to firmly grip the tissue to be sutured and to pinch the tissue into a desirable configuration to receive the purse string sutures. To clamp the tissue into the desired configuration, the successive teeth on each jaw are alternately pointed and smooth with the pointed teeth on each jaw being opposed to the smooth teeth on the other jaw. Preferably, the pointed teeth on each jaw are higher than the smooth teeth on the same jaw. Also, the successive teeth on each jaw are separated by valleys which receive the tissue clamped between the jaws. A needle passage is formed in each jaw and extends through the teeth on the jaw for guiding a needle attached to a purse string suture therethrough. Preferably, the needle passages extend through the teeth between the valleys on opposite sides of each tooth to guide the needles through the tissue. Each valley is defined by a steeply sloped wall on one of said pointed teeth and a gradually sloped wall on one of said smooth teeth. The arrangement of alternately pointed and smooth teeth allows the jaws to firmly clamp the tissue in a fixed position and provides for a smooth flow of tissue into the valleys between the teeth.

According to one aspect of the invention, the purse string suture instrument comprises a pair of jaws each having a plurality of teeth for clamping the tissue therebetween, a needle passage formed in each of the jaws and extending through the teeth on each jaw, a pair of needles mounted on the jaws for movement through the passages, a purse string suture attached to each of the needles, means for advancing the needles along the jaws to move the purse string sutures through the needle passages and into the tissue, and means on each of the jaws for capturing the needles after advancement of the needles through the needle passages. Preferably, a pair of needle retainers is located adjacent to the ends of the jaws for capturing the respective needles on the jaws. The needle retainers comprise a pair of tabs mounted in slots adjacent to the ends of the jaws and provided with openings aligned with the respective needle passages in the jaws. The needles include annular grooves which are captured by the tabs when the needles are advanced into the openings. Since the needles are retained in the jaws of the instrument, the need for a surgeon to manually retrieve the needles from the surgical site is avoided.

According to another aspect of the invention, the purse string suture instrument includes a needle advancing mechanism comprising a pair of tubular sleeves slidably mounted on the tissue clamping jaws for movement along the needle passages. The tubular sleeves are engageable with the needles and receive the purse string sutures therein. The tubular sleeves guard the purse string sutures against damage as the sutures are drawn through the needle passages in the teeth. The instrument includes actuators connected to the tubular sleeves which are operable simultaneously or independently to allow the purse string sutures to be selectively applied to the tissue.

In another embodiment of the invention, the purse string suture instrument includes a pair of jaws each having a plurality of teeth for clamping the tissue therebetween, a needle passage formed in each of the jaws and extending through the teeth on each jaw, a pair of needles mounted on the jaws for movement through the passages, a purse string suture attached to each of the needles, means for advancing the needles along the jaws to move the purse string sutures through the needle passages and into the tissue, and knife means mounted for movement relative to the jaws for cutting the tissue adjacent to the purse string sutures threaded therein. Preferably, a knife passage is formed in each of the tissue clamping jaws and extends along a path adjacent to the needle passage therein. A knife blade is slidably received in the knife passages for movement relative to the jaws. The instrument includes an actuator for advancing the needles and the knife blade along the jaws. The purse string sutures are moved through the needle passages and threaded into the tissue and the knife blade is moved along the knife passages to cut the tissue adjacent to purse string sutures therein.

In a modified embodiment of the purse string suture instrument, a tissue clamp is releaseably mounted on the tissue clamping jaws. The tissue clamp is clamped onto the tubular tissue when the jaws of the purse string suture instrument are closed and is disengaged from the jaws when the instrument is opened. The tissue clamp includes first and second clamping members adapted to interlock when the jaws are closed to clamp the tissue between the clamping members. Preferably, the two-part tissue clamp comprises a U-shaped clamping member mounted on one of the jaws having a pair of upstanding arms at its opposite ends and a clamping bar mounted on the other jaw and adapted to interlock with the upstanding arms when the jaws are closed. The upstanding arms of the U-shaped clamping member provide a tissue guide for locating the tissue between the working or toothed portions of the jaws. The purse string suture instrument allows the tissue clamp to be applied to a tubular section of tissue prior to the threading of purse string sutures into the tissue. After the clamp is applied, the tissue is dissected along the edge of the clamp adjacent to the purse string sutures threaded into the tissue. This embodiment avoids the need to use another surgical instrument, e.g., an L-shaped clamp, for clamping the tissue to be dissected.

The modified embodiment of the purse string suture instrument which supports the tissue clamp is particularly useful for the removal of a damaged section from an elongated tubular tissue, e.g., intestinal tissue in a bowel resection. By using two separate instruments, a pair of tissue clamps is applied to opposite ends of the damaged section of tissue and purse string sutures are threaded into the healthy tissue adjacent to the tissue clamps. The damaged section is severed along the edges of the clamps facing the healthy tissue. The severed ends of the healthy tissue are closed by tightening and wrapping the purse string sutures threaded therein. The damaged tissue section, which is clamped at both ends, is removed, and the healthy, purse-stringed portions of tissue are anastomosed by using a circular anastomosis instrument.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view showing the purse string suture instrument of the present invention with its jaws open;

FIG. 2 is a plan view of the purse string instrument with its jaws closed;

FIG. 3 is a top view of the purse string suture instrument;

FIG. 7 is an enlarged section taken along line 7—7 of FIG. 2;

FIG. 8 is an enlarged section taken along line 8—8 of FIG. 2;

FIG. 9 is an enlarged, partially cutaway view showing an actuator for one of the needles and purse string sutures;

FIG. 10 is an enlarged fragmentary view of the jaws illustrating the needles and purse string sutures advanced to the front of the jaws;

FIG. 11 is a plan view of another embodiment of the purse string suture instrument provided with a tissue cutting knife;

FIG. 12 is a top view of the purse string suture instrument of FIG. 11;

FIG. 13 is a perspective view showing another embodiment of the purse string instrument which supports a two-piece tissue clamp on the jaws of the instrument;

FIG. 14 illustrates a dissected section of tubular tissue after operation of the purse string suture instrument of FIG. 13 to apply the tissue clamp and purse string sutures to the tissue:

FIG. 15 is an enlarged side view of the jaws and the tissue clamp of FIG. 13,

FIG. 16 is an enlarged end view of the jaws and the tissue clamp of FIG. 15;

FIG. 17 is an enlarged top view of the jaws and the tissue clamp of FIG. 15; and FIG. 18 is an enlarged bottom view of the jaws and the tissue clamp of FIG. 15.

DETAILED DESCRIPTION OF PREFERRED EMBODIMENTS

Figure 4:
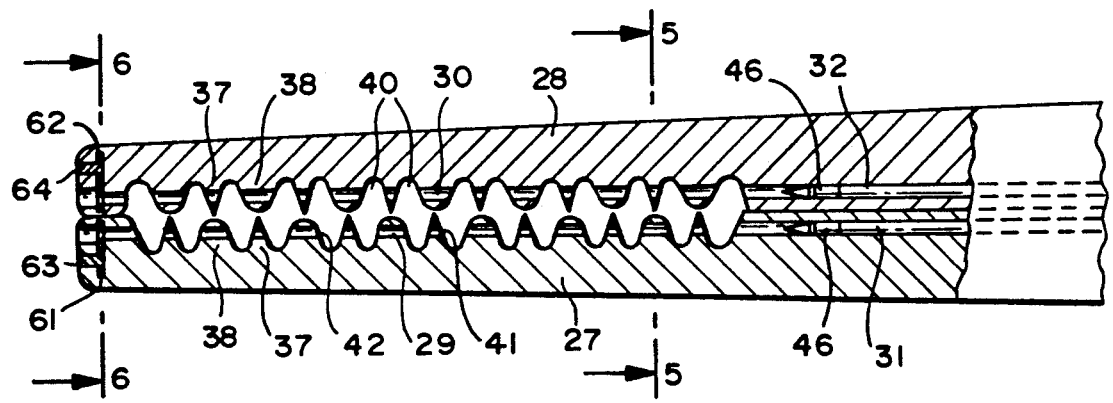
FIG. 4 is an enlarged, partially cutaway view showing the jaws of the purse string suture instrument.

Referring to FIG. 1, the present invention is embodied in a surgical instrument, generally 20, which is used to apply purse string sutures in the course of surgery on human tissue. This instrument is particularly suitable for applying purse string sutures to intestinal tissue which is generally tubular in shape.

A preferred embodiment of the surgical instrument 20 comprises a pair of elongated handles 21 and 22 pivotally connected by a pivot pin 23 in a scissors-like arrangement. A pair of finger grips or rings 24 and 25 is provided at the rear of handles 21 and 22, respectively, to facilitate the handling and operation of the surgical instrument 20 by a surgeon. A pair of latch arms 26 is provided on the handles 21 and 22 adjacent to finger grips 24 and 25. The latch arms 26 are adapted to interlock when the handles 21 and 22 are pivoted together to a closed position.

As shown in FIGS. 1 and 2, the front portions of handles 21 and 22 form a pair of tissue clamping jaws 27 and 28, respectively, which are tapered in the forward direction. As shown in FIG. 3, the jaws 27 and 28 are curved to one side so that the front portions of the jaws are oriented at an angle of approximately 45 degrees to the rear portions of the handles 21 and 22.

Referring to FIG. 4, both jaws 27 and 28 are formed with a plurality of teeth for clamping the tissue therebetween when the handles 21 and 22 are pivoted together. Each jaw has a toothed portion including a plurality of pointed teeth 37 and a plurality of smooth teeth 38 arranged such that the successive teeth on each jaw are alternately pointed and smooth with the pointed teeth 37 on each jaw being opposed to the smooth teeth 38 on the other jaw. As shown in FIG. 10, on both jaws 27 and 28, the pointed teeth 37 are higher than the smooth teeth 38. The pointed teeth 37 and smooth teeth 38 on each jaw are separated by valleys 40 which receive the tissue clamped between the jaws 27 and 28. Each valley 40 is defined by a steeply sloped wall 41 on the pointed tooth 37 and a gradually sloped wall 42 on the smooth tooth 38 which are located on opposite sides of the valley 40. Preferably, the steeply sloped wall 41 is sloped at an angle of approximately 60 degrees and the gradually sloped wall 42 is sloped at an angle of approximately 45 degrees relative to the axial direction of the needle passages 29 and 30. The sloped walls 41 and 42 allow the tissue pinched by the teeth 37 and 38 to extend substantially to the bottom of each valley 40.

A pair of longitudinal needle passages 29 and 30 (FIGS. 2 and 4) is formed in the jaws 27 and 28, respectively. The needle passage 29 extends through the teeth 37 and 38 on the first jaw 27 between the valleys 40 on opposite side of the teeth. Similarly, the needle passage 30 extends through the teeth 37 and 38 on the second jaw 28 between the valleys 40 on opposite sides of the teeth.

As shown in FIGS. 1 and 2, the instrument 20 includes a pair of elongated tubular sleeves 31 and 32 which are slidably mounted on the handles 21 and 22 and extend into the needle passages 29 and 30, respectively. The tubular sleeves 31 and 32 are attached at the rear to a pair of manually operated actuators or slides 33 and 34, respectively, which are slidably mounted in a pair of elongated channels 35 formed in the handles 21 and 22. The tubular sleeves 31 and 32 are supported by a plurality of support blocks 36 which are spaced apart and slidably mounted in the channels 35 formed in the handles 21 and 22. Also, the tubular sleeves 31 and 32 are arranged in a crisscross and are slidably received by the pivot pin 23.

As shown in FIG. 7, the channel 35 on handle 22 is formed in the shape of a keyway to slidably receive a T-shaped leg 44 depending from each support block 36. On the other handle 21, the channel 35 and support blocks 36 are similarly formed. As shown FIG. 8, the actuator 34 on handle 22 includes a T-shaped base 45 which is slidably received in the keyway-shaped channel 35 formed in the handle 22. On the other handle 21, the actuator 33 is similarly formed and slidably received in the keyway-shaped channel 35.

Referring to FIG. 4, a pair of needles 46 is mounted on jaws 27 and 28 for movement through needle passages 29 and 30. A pair of purse string sutures 47 (FIGS. 9 and 10) is attached to the needles 46 and the sutures 47 extend rearwardly through the tubular sleeves 31 and 32. Each needle 46 has a pointed front end with an annular groove 48 (FIG. 9) formed adjacent to the front end of the needle. The annular grooves 48 allow the needles 46 to be captured by a pair of needle retainers 61 and 62 located adjacent to the front ends of the jaws 27 and 28, respectively.

Figure 5:
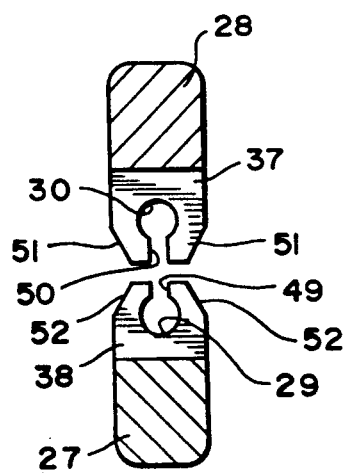
FIG. 5 is a vertical section of the jaws taken along line 5—5 of FIG. 4.

As shown in FIG. 5, each of the pointed teeth 37 and the smooth teeth 38 on the lower jaw 27 has a vertical slot 49 which extends from the tooth surface to the needle passage 29. Similarly, each of the pointed teeth 37 and the smooth teeth 38 on the upper jaw 28 has a vertical slot 50 which extends from the tooth surface to the needle passage 30. The slots 49 and 50 allow the purse string sutures 47 to be removed from the needle passages 29 and 30 when the jaws 27 and 28 are pivoted apart. Preferably, the outside edges 51 of the pointed teeth 37 and the outside edges 52 of the smooth teeth 38 are beveled inwardly.

Figure 6:
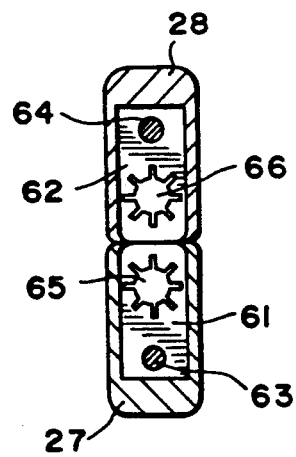
FIG. 6 is a vertical section of the jaws taken along line 6—6 of FIG. 4.

Referring to FIGS. 4 and 6, the needle retainers 61 and 62 comprise a pair of flat, tab-like members mounted in transverse slots adjacent to the front ends of jaws 27 and 28. As shown in FIG. 6, the tab-like retainers 61 and 62 are secured to the jaws 27 and 28 by pins 63 and 64, respectively. The tab-like retainers 61 and 62 include circular openings 65 and 66 which are aligned with the needle passages 29 and 30, respectively. The openings 65 and 66 are made expandable by a plurality of radial slits formed in the tab-like retainers 61 and 62. When the pointed needles 46 enter the openings 65 and 66, the needle retainers 61 and 62 capture the needles 46 by the annular grooves 48 formed therein.

In the operation of the purse string suture instrument 20, the jaws 27 and 28 are opened by grasping finger grips 24 and 25 and moving handles 21 and 22 apart. The instrument 20 is positioned with its open jaws 27 and 28 on opposite sides of a tubular piece of tissue. Then, the jaws 27 and 28 are closed by grasping finger grips 24 and 25 and moving handles 21 and 22 together to clamp the tissue between the jaws 27 and 28. The handles 21 and 22 are latched together by the latch arms 26 to hold the jaws 27 and 28 closed. As shown in FIG. 10, the tissue is pinched between the opposed pointed teeth 37 and smooth teeth 38 and urged substantially to the bottom of the valleys 40 located between the adjacent teeth on each of the jaws 27 and 28. The tissue is gathered into a configuration such that the tissue in each valley is pierced by the corresponding needle 46 and suture 47 when the needle 46 is advanced.

With the jaws 27 and 28 closed, one or both actuators 33 and 34 are moved forwardly to advance the corresponding tubular sleeves 31 and 32 along the needle passages 29 and 30, respectively. The needles 46 are engaged by the front ends of the tubular sleeves 31 and 32 and together with the sutures 47 are advanced along the needle passages 29 and 30 which extend through the alternating pointed teeth 37 and smooth teeth 38 on the jaws 27 and 28. As a result, the tubular sleeves 31 and 32, the needles 46 and the purse string sutures 47 are advanced through the tissue located in the valleys 40 between the pointed teeth 37 and the smooth teeth 38 on the respective jaws 27 and 28. Because the purse string sutures 47 are received in the tubular sleeves 31 and 32, the sutures 47 are protected against possible damage during the advancement of the needles 46. The tubular sleeves 31 and 32 are advanced by the actuators 33 and 34 until the needles 46 are captured by the retainers 61 and 62 at the front ends of the jaws 27 and 28. The advance of the needles 46 is stopped when the annular grooves 48 are captured in the openings 65 and 66 (FIG. 6) formed in the needle retainers 61 and 62.

Next, as shown in FIG. 10, the tubular sleeves 31 and 32 are retracted through the needle passages 29 and 30 by sliding the actuators 33 and 34 rearwardly along the handles 21 and 22. The needles 46 remain captured by the needle retainers 61 and 62 and the purse string sutures 47 remain threaded through the tissue clamped between the jaws 27 and 28. Then, a surgical knife (not shown) is advanced along the concave sides of the jaws 27 and 28 to sever the tissue. Alternatively, the tissue can be severed before the actuators 33 and 34 retract the tubular sleeves 131 and 132. When the jaws 27 and 28 are opened to unclamp the tissue, the slots 29 and 30 (FIG. 5) allow the purse string sutures to be removed from the teeth 37 and 38. Thereafter, the purse string sutures 47 are severed from the needles 46 and are tightened and wrapped about the tissue by the surgeon to complete the purse stringing procedure.

Referring to FIGS. 11 and 12, a second embodiment of the purse string suture instrument 120 comprises a pair of elongated handles 121 and 122 pivotally connected by a pivot pin 123 in a scissors-like arrangement. A pair of finger grips or rings 124 and 125 is provided at the rear of handles 121 and 122, respectively, to facilitate the handling and operation of the surgical instrument 120 by a surgeon. A pair of latch arms 126 is provided on the handles 121 and 122 adjacent to finger grips 124 and 125. The latch arms 126 are adapted to interlock when the handles 121 and 122 are pivoted together to a closed position.

As shown in FIG. 11, the front portions of handles 121 and 122 form a pair of tissue clamping jaws 127 and 128, respectively, which are tapered in the forward direction. As shown in FIG. 12, the jaws 127 and 128 are curved to one side and terminate in straight front portions which are oriented at an angle of approximately 75 degrees to the rear portions of the handles 121 and 122.

Referring to FIG. 11, both jaws 127 and 128 are formed with a plurality of teeth for clamping the tissue therebetween when the handles 121 and 122 are pivoted together. Like jaws 27 and 28 (FIGS. 1 and 2) described above, each of the jaws 127 and 128 has a toothed portion including a plurality of pointed teeth and a plurality of smooth teeth arranged such that the successive teeth on each jaw are alternately pointed and smooth with the pointed teeth on each jaw being opposed to the smooth teeth on the other jaw. The pointed and smooth teeth on the jaws 127 and 128 (FIG. 11) have essentially the same structure as the teeth 37 and 38 (FIG. 10) described above.

A pair of longitudinal needle passages 129 and 130 (FIG. 11) is formed in the jaws 127 and 128, respectively. The needle passage 129 extends through the alternately pointed and smooth teeth on the first jaw 127. Similarly, the needle passage 130 extends through the alternately pointed and smooth teeth on the second jaw 128.

As shown in FIG. 11, the instrument 120 includes a pair of elongated tubular sleeves 131 and 132 which are slidably mounted on the handles 121 and 122 and extend into the needle passages 129 and 130, respectively. The tubular sleeves 131 and 132 are attached at the rear to a pair of needle actuators or slides 133 and 134, respectively, which are slidably mounted in a pair of elongated channels 135 formed in the handles 121 and 122. The tubular sleeves 131 and 132 are supported by a plurality of support blocks 136 which are spaced apart and slidably mounted in the channels 135 formed in the handles 121 and 122. The actuators 133 and 134, the channels 135, and the support blocks 136 are similar in structure to the actuators 33 and 34, the channels 35, and the support blocks 36 (FIG. 2) described above.

Referring to FIG. 11, a pair of needles 146 is mounted on jaws 127 and 128 for movement through the needle passages 129 and 130. A pair of purse string sutures 147 is attached to the needles 146 and the sutures 147 extend rearwardly through the tubular sleeves 131 and 132. Each needle 146 has essentially the same structure as the needle 46 (FIG. 9) described above. Also, the jaws 127 and 128 are provided with a pair of needle retainers (not shown) which are similar in structure to the needle retainers 61 and 62 (FIG. 10) and which operate in a similar manner to capture the needles 146 when the sleeves 131 and 132 are advanced.

The purse string suture instrument 120 includes an elongated flexible tissue cutting knife blade 150 which is slidably received in a pair of longitudinal slots 151 and 152 formed in the jaws 127 and 128, respectively. The front of the knife blade 150 includes a sharp beveled edge 154 (FIG. 11) for cutting the tissue clamped between the jaws 127 and 128. The rear of the knife blade 150 is secured to a knife actuator or slide 155 which is slidably mounted on the purse string suture instrument 120 by an elongated support plate 156 (FIG. 12) secured to the opposite side of one of the handles 131 and 132 from the knife blade 150. The support plate 156 includes a longitudinal slot (not shown) for slidably receiving a bolt 157 which is secured to the knife actuator 155. The knife blade 150 is fastened to the knife actuator 155 by a screw 158. In addition, a screw 159 is secured to each of the needle actuators 133 and 134. Each screw 159 is received in a lateral slot 160 formed in the knife actuator 155 to couple the needle actuators 133 and 134 to the knife actuator 155 for simultaneous movement therewith. Preferably, the knife blade 150 is arranged to cut the tissue at a distance of several millimeters from the concave sides of the jaws 127 and 128.

In the operation of the purse string suture instrument 120, the jaws 127 and 128 are opened by grasping finger grips 124 and 125 and moving handles 121 and 122 apart. The instrument 120 is positioned with its open jaws 127 and 128 on opposite sides of a tubular piece of tissue. Then, the jaws 127 and 128 are closed by grasping finger grips 124 and 125 and moving handles 121 and 122 together to clamp the tissue between the jaws 127 and 128. The handles 121 and 122 are latched together by the latch arms 126 to hold the jaws 127 and 128 closed. The tissue is pinched between the toothed portions of the jaws 127 and 128.

With the jaws 127 and 128 closed, the knife actuator 155 is moved forwardly to simultaneously advance the needle actuators 133 and 134 which, in turn, advance the corresponding tubular sleeves 131 and 132 along the needle passages 129 and 130, respectively. The needles 146 are engaged by the front ends of the tubular sleeves 131 and 132 and together with the sutures 147 are advanced along the needle passages 129 and 130 which extend through the alternating pointed teeth and smooth teeth on the jaws 127 and 128. As a result, the tubular sleeves 131 and 132, the needles 146 and the purse string sutures 147 are advanced through the tissue located between the toothed portions of the jaws 127 and 128. Because the purse string sutures 147 are received in the tubular sleeves 131 and 132, the sutures 147 are protected against possible damage during the advancement of the needles 146. The tubular sleeves 131 and 132 are advanced by the needle actuators 133 and 134 until the needles 146 are captured by the retainers (not shown) at the front ends of the jaws 127 and 128. At the same time, the knife blade 150 is advanced along the longitudinal passages 151 and 152 by the knife actuator 155 to cut the tissue along a path parallel to the needle passages 129 and 130.

After the needles 146 and sutures 147 are advanced and the tissue is cut by the knife blade 150, the knife actuator 155 is returned to its initial position to retract the tubular sleeves 131 and 132 through the needle passages 129 and 130 and to retract the knife blade 150 along the passages 151 and 152. The needles 146 remain captured by the needle retainers (not shown) at the front of the jaws 127 and 128 and the purse string sutures 147 remain threaded through the tissue clamped between the jaws 127 and 128. Next, the jaws 127 and 128 are opened to unclamp the tissue The purse string sutures 147 are severed from the needles 146 and are tightened and wrapped about the tissue by the surgeon to complete the purse stringing procedure.

Referring to FIG. 13, a modification is shown which includes a two-part tissue clamp 80 releaseably mounted on the jaws of the purse string suture instrument. The tissue clamp 80 is adapted to clamp onto the tissue when the purse string suture instrument is closed and to disengage from the jaws when the instrument is opened. This modification is applicable to both embodiments described above, i.e., the purse string suture instrument 20 of FIGS. 1–10 and the purse string suture instrument 120 of FIGS. 11 and 12. By way of example, the tissue clamp 80 is described below in connection with the purse string suture instrument 20 (FIGS. 1–10).

As shown in FIGS. 15–18, the two-part tissue clamp 80 comprises an elongated U-shaped member 81 mounted on the jaw 27 and an elongated clamping bar 82 mounted on the jaw 28. The U-shaped clamping member 81 includes a pair of upstanding arms 83 at its opposite ends which include inwardly facing prongs 84. A pair of notches 85 (FIG. 13) is formed at the opposite ends of the clamping bar 82 for receiving the arms 83 of the U-shaped clamping member 81. When the arms 83 are inserted into the notches 85, the arms 83 initially flex outwardly to receive the bar 82 therebetween. Then, the arms 83 flex inwardly and the prongs 84 snap over the bar 82 (FIG. 15) to hold the U-shaped clamping member 81 and the bar 82 together and to clamp the tissue therebetween. To enable the clamp 80 to firmly grip the tissue, a plurality of teeth 87 is formed on the U-shaped clamping member 81 and a plurality of teeth 88 is formed on the clamping bar 82.

Referring to FIG. 13, the U-shaped clamping member 81 is releasably held by a plurality of brackets 91 which are spaced longitudinally along the jaw 27. Similarly, the clamping bar 82 is releasably held by a plurality of brackets 92 which are spaced longitudinally along the jaw 28. With the U-shaped clamping member 81 mounted on the jaw 27, the upstanding arms 83 serve as a tissue guide for locating the tissue in a desired position between the toothed portions of the jaws 27 and 28.

In the operation of the purse string suture instrument of FIG. 13, the jaws 27 and 28 are positioned on opposite sides of an elongated tubular tissue, e.g., intestinal tissue, which is located between the arms 83 of the U-shaped tissue clamping member 81. When the jaws 27 and 28 are closed, the tubular tissue is clamped by the toothed portions of the jaws 27 and 28. Also, the arms 83 of the U-shaped clamping member 81 are received in the notches 85 of the clamping bar 82 and the prongs 84 snap over the bar 82. Thus, the tissue clamp 80 (FIG. 14) is clamped across the tubular tissue. The teeth 87 and 88 enable the tissue clamp 80 to firmly grip the tissue and to remain in a fixed position thereon. Then, the purse string suture instrument is actuated to thread the purse string sutures into the tissue clamped between the jaws 27 and 28.

Next, as shown in FIG. 14, the tubular tissue is dissected on the distal side of the tissue clamp 80 to sever a proximal portion 95 of the tubular tissue which is clamped by the tissue clamp 80 from a distal portion 96 of the tubular tissue into which the purse string sutures 47 are threaded. If the purse string suture instrument 20 is used, the tissue cutting is performed manually by using a separate knife which is moved across the tissue on the distal side of the tissue clamp 80. If the purse string suture instrument 120 (FIGS. 11 and 12) is used, the tissue cutting is performed by the knife blade 150 simultaneously with the threading of the purse string sutures into the tissue. After the tissue cutting is completed, the purse string sutures 47 are tightened and wrapped about the tissue by the surgeon to close the severed end of the distal portion 96 of the tubular tissue.

The purse string suture instrument of FIG. 13 can be used for the removal of a damaged section of tubular tissue from healthy tissue, e.g., in a bowel resection. Referring to FIG. 14, a first purse string suture operation is performed at one end of the damaged section 95 of tubular tissue using the purse string suture instrument provided with the tissue clamp 80 on its jaws. As a result, one end of the damaged section 95 of tubular tissue is closed by a first tissue clamp 80. The damaged section 95 is severed from the healthy portion 96 of the tubular tissue along the edge of the clamp 80 facing the healthy tissue, either by using a separate surgical knife or by the instrument itself (FIGS. 11–12). The severed end of the healthy portion 96 of tubular tissue is closed by the purse string sutures 47 which are tightened and wrapped by the surgeon about the severed end of the tissue.

Similarly, at the other end of the damaged section 95 of tubular tissue, a second purse string suture operation is performed using the same type of purse string suture instrument provided with another tissue clamp 80. As a result, the other end of the damaged section 95 of tubular tissue is closed by a second tissue clamp 80 (not shown). The damaged section 95 is severed from the healthy tubular tissue along the edge of the second clamp 80 facing the healthy tissue. The severed end of the healthy portion of the tubular tissue is closed by another set of purse string sutures which are tightened and wrapped by the surgeon about the tissue. The damaged tissue section 95, which is clamped at both ends, is removed and the healthy, purse-stringed portions are anastomosed by using a circular anastomosis instrument (not shown).

Preferably, the purse string suture instrument 20 (FIGS. 1-10) and the instrument 120 (FIGS. 11-12) are one-shot disposable surgical devices. Also, the modified embodiment of FIG. 13 is a disposable surgical device.

The invention in its broader aspects is not limited to the specific details of the preferred embodiments shown and described, and those skilled in the art will recognize that the invention can be practiced with modification within the spirit and scope of the appended claims.

I claim:

1. A surgical instrument for applying purse string sutures to tissue, comprising:
   a pair of jaws each having a plurality of teeth for clamping the tissue therebetween;
   a needle passage formed in each of said jaws and extending through the teeth on each jaw;
   a pair of needles mounted on said jaws for movement through said passages;
   a purse string suture attached to each of said needles;
   means for advancing said needles along said jaws to move said purse string sutures through said needle passages and into said tissue; and
   means on each of said jaws for capturing said needles after advancement of said needles through said needle passages.

2. The surgical instrument of claim 1, wherein said needle capturing means includes:
   a pair of needle retainers located adjacent to the ends of said jaws for capturing the respective needles on said jaws.

3. The surgical instrument of claim 2, wherein said needle retainers comprise:
   a pair of tabs mounted in slots adjacent to the ends of said jaws, said tabs including openings aligned with the respective needle passages in said jaws; and
   said needles include annular grooves which are captured by said tabs as said needles are advanced into said openings.

4. A surgical instrument for applying purse string sutures to tissue, comprising:
   a pair of jaws each having a plurality of teeth for clamping the tissue therebetween;
   a needle passage formed in each of said jaws and extending through the teeth on each jaw;
   a pair of needles mounted on said jaws for movement through said passages;
   a purse string suture attached to each of said needles;
   means for advancing said needles along said jaws to move said purse string sutures through said needle passages and into said tissue; and
   said needle advancing means including a pair of tubular sleeves slidably mounted on said jaws for movement along said passages, said sleeves being engageable with said needles and receiving said purse string sutures therein.

5. The surgical instrument of claim 4, which includes:
   means on each of said jaws for capturing said needles after advancement of said needles through said needle passages.

6. The surgical instrument of claim 5, wherein said needle capturing means includes:
   a pair of needle retainers located adjacent to the ends of said jaws for capturing the respective needles on said jaws.

7. The surgical instrument of claim 4, wherein said needle retainers comprise:
   a pair of tabs mounted in slots adjacent to the ends of said jaws, said tabs including openings aligned with the respective needle passages in said jaws; and
   said needles include annular grooves which are captured by said tabs as said needles are advanced into said openings.

8. A surgical instrument for applying purse string sutures to tissue, comprising:
   a pair of jaws each having a plurality of teeth for clamping the tissue therebetween;
   a needle passage formed in each of said jaws and extending through the teeth on each jaw;
   a pair of needles mounted on said jaws for movement through said passages;
   a purse string suture attached to each of said needles;
   means for advancing said needles along said jaws to move said purse string sutures through said needle passages and into said tissue; and wherein
   successive teeth on each jaw are alternately pointed and smooth, said pointed teeth on each jaw being opposed to said smooth teeth on the other jaw.

9. The surgical instrument of claim 8, wherein:
   said pointed teeth on each jaw are higher than the smooth teeth on the same jaw.

10. The surgical instrument of claim 8, wherein:
    said successive teeth on each jaw are separated by valleys which receive the tissue clamped between said jaws.

11. The surgical instrument of claim 10, wherein:
    said needle passages extend through said teeth between the valleys on opposite sides of each tooth to guide said needles through the tissue when the sleeves are advanced through said passages.

12. A surgical instrument for applying purse string sutures to tissue, comprising:
    a pair of elongated handles pivotally connected together, said handles supporting a pair of jaws each having a plurality of teeth for clamping the tissue therebetween when said handles are pivoted together;
    a needle passage formed in each of said jaws and extending through said teeth on each jaw;
    a pair of needles mounted on said jaws for movement through said passages;
    a purse string suture attached to each of said needles;
    a pair of elongated tubular sleeves slidably mounted on said handles and extending into said passages, said sleeves being engageable with said needles and receiving said purse string sutures therein; and
    a pair of actuators slidably mounted on said handles for moving said sleeves longitudinally along said handles to advance said needles and said purse string sutures through said needle passages when said actuators are advanced and to withdraw said sleeves away from said needles when said actuators are retracted.

13. The surgical instrument of claim 12, wherein:
    said actuators are operable independently to allow said purse string sutures to be selectively applied to the tissue.

14. The surgical instrument of claim 12, which includes:
    means on each of said jaws for capturing said needles after advancement of said needles through said needle passages.

15. The surgical instrument of claim 14, which includes:
a pair of needle retainers located adjacent to the ends of said jaws for capturing the respective needles on said jaws.

16. The surgical instrument of claim 15, wherein said needle retainers comprise:
a pair of tabs mounted in slots adjacent to the ends of said jaws, said tabs including openings aligned with the respective needle passages in said jaws; and
said needles include annular grooves which are captured by said tabs as said needles are advanced into said openings.

17. The surgical instrument of claim 12, wherein:
successive teeth on each jaw are alternately pointed and smooth, said pointed teeth on each jaw being opposed to said smooth teeth on the other jaw.

18. The surgical instrument of claim 17, wherein:
said pointed teeth on each jaw are higher than the smooth teeth on the same jaw.

19. The surgical clip of claim 17, wherein:
said successive teeth on each jaw are separated by valleys which receive the tissue clamped between said jaws.

20. The surgical instrument of claim 19, wherein:
said needle passages extend through said teeth between the valleys on opposite sides of each tooth to guide said needles through the tissue when the sleeves are advanced through said passages.

21. The surgical instrument of claim 20, wherein:
each valley is defined by a steeply sloped wall on one of said pointed teeth and a gradually sloped wall on one of said smooth teeth.

22. A surgical instrument for applying purse string sutures to tissue, comprising:
a pair of jaws each having a plurality of teeth for clamping the tissue therebetween;
a needle passage formed in each of said jaws and extending through the teeth on each jaw for guiding a needle attached to a purse string suture therethrough; and wherein
successive teeth on each jaw are alternately pointed and smooth, said pointed teeth on each jaw being opposed to said smooth teeth on the other jaw.

23. The surgical instrument of claim 22, wherein:
said pointed teeth on each jaw are higher than the smooth teeth on the same jaw.

24. The surgical instrument of claim 22, wherein:
said successive teeth on each jaw are separated by valleys which receive the tissue clamped between said jaws 25. The surgical instrument of claim 24, wherein:
said needle passages extend through said teeth between the valleys on opposite sides of each tooth to guide said needles through the tissue when said sleeves are advanced through said passages 26. The surgical instrument of claim 25, wherein:
each valley is defined by a steeply sloped wall on one of said pointed teeth and a gradually sloped wall on one of said smooth teeth 27. A surgical instrument for applying purse string sutures to tissue, comprising:
a pair of jaws each having a plurality of teeth for clamping the tissue therebetween;
a needle passage formed in each of said jaws and extending through the teeth on each jaw for guiding a needle attached to a purse string suture therethrough; and
knife means mounted for movement relative to said jaws for cutting the tissue adjacent to the purse string sutures threaded into the tissue 28. A surgical instrument for applying purse string sutures to tissue, comprising
a pair of jaws each having a plurality of teeth for clamping the tissue therebetween;
a needle passage formed in each of said jaws and extending through the teeth on each jaw;
a pair of needles mounted on said jaws for movement through said passages;
a purse string suture attached to each of said needles;
a knife passage formed in each of said jaws and extending along a path adjacent to said needle passage therein;
a knife blade slidably received in said knife passages for movement relative to said jaws; and
means for advancing said needles and said knife blade along said jaws to move said purse string sutures through said needle passages and into said tissue and to move said knife blade along said knife passages to cut the tissue adjacent to the purse string sutures threaded therein.

29. The surgical instrument of claim 28, wherein:
said advancing means includes a pair of tubular sleeves slidably mounted on said jaws for movement along said needle passages, said sleeves being engageable with said needles and receiving said purse string sutures therein 30. The surgical instrument of claim 29, wherein:
said advancing means includes an actuator connected to said tubular sleeves and to said knife blade for simultaneously advancing said needles and said knife blade along said passages in said jaws.

31. A surgical instrument for applying purse string sutures to tissue, comprising:
a pair of jaws each having a plurality of teeth for clamping the tissue therebetween;
a needle passage formed in each of said jaws and extending through the teeth on each jaw for guiding a needle attached to a purse string suture therethrough; and
a tissue clamp releaseably mounted on said jaws and applied to the tissue when the jaws are closed.

32. A surgical instrument for applying purse string sutures to tissue, comprising:
a pair of jaws each having a toothed portion including a plurality of teeth for clamping the tissue therebetween;
a needle passage formed in each of said jaws and extending through the teeth on each jaw;
a pair of needles mounted on said jaws for movement through said passages;
a purse string suture attached to each of said needles;
means for advancing said needles along said jaws to move said purse string sutures through said needle passages and into said tissue; and
a tissue clamp releaseably mounted on said jaws, said tissue clamp including first and second clamping members adapted to interlock when said jaws are closed to clamp the tissue between said clamping members.

33. The surgical instrument of claim 32, wherein:
said tissue clamp includes a U-shaped clamping member mounted on one of said jaws having a pair of upstanding arms at its opposite ends and a clamping bar mounted on the other jaw and adapted to interlock with said arms when said jaws are closed.

34. The surgical instrument of claim 33, wherein:
said upstanding arms of said U-shaped clamping member provide a tissue guide for locating the tissue between said toothed portions of said jaws.

* * * * *